United States Patent [19]

DeVera

[11] Patent Number: 5,977,411
[45] Date of Patent: Nov. 2, 1999

[54] CATALYTIC HYDROGENERATION OF NITROBENZENE TO 4-AMINODIPHENYLAMINE IN THE PRESENCE OF A HYDROXYL COMPOUND AND A SOLVENT

[75] Inventor: Antonio L. DeVera, Ballwin, Mo.

[73] Assignee: Flexsys America L.P., Akron, Ohio

[21] Appl. No.: 08/872,030

[22] Filed: Jun. 10, 1997

[51] Int. Cl.[6] .......................... C07C 209/00; C07C 211/00
[52] U.S. Cl. ..................... 564/397; 564/398; 564/408; 564/420; 564/421; 564/423; 564/433; 564/434
[58] Field of Search ................................... 564/398, 397, 564/408, 420, 421, 423, 433, 434

[56] References Cited

U.S. PATENT DOCUMENTS 5,117,063 5/1992 Stern et al. ............................ 564/398
5,453,541 9/1995 Stern et al. ............................ 564/398

Primary Examiner—Jose' G. Dees
Assistant Examiner—Alton Pryor
Attorney, Agent, or Firm—Louis A. Morris

[57] ABSTRACT

This invention provides a method for preparing 4-ADPA by charging nitrobenzene into a reaction zone under hydrogen pressure in the presence of a strong organic base and a catalyst for hydrogenation. The method provides the convenience and economy of a one-step process, while producing improved yields and selectivities. The invention further provides for various embodiments of the foregoing which are suitable for the production of 4-ADPA, and the hydrogenation or reductive alkylation to produce PPD. Important to the invention are the molar ratios of aniline to nitrobenzene and nitrobenzene to the strong organic base and the choice and use of hydrogenation catalyst.

25 Claims, No Drawings

CATALYTIC HYDROGENERATION OF NITROBENZENE TO 4-AMINODIPHENYLAMINE IN THE PRESENCE OF A HYDROXYL COMPOUND AND A SOLVENT

BACKGROUND OF THE INVENTION

This invention relates to a method of making 4-aminodiphenylamine (4-ADPA), an important intermediate in the production of substituted paraphenylenediamine (PPD) antidegradants for polymers, especially rubber.

It is known to prepare 4-ADPA by way of a nucleophilic aromatic substitution mechanism, wherein an aniline derivative replaces halide. This method involves preparation of a 4-ADPA intermediate, namely 4-nitrodiphenylamine (4-NDPA) followed by reduction of the nitro moiety. The 4-NDPA is prepared by reacting p-chloronitrobenzene with an aniline derivative, such as formanilide or an alkali metal salt thereof, in the presence of an acid acceptor or neutralizing agent, such as potassium carbonate, and, optionally, utilizing a catalyst. See, for example, U.S. Pat. Nos. 4,187, 248; 4,683,332; 4,155,936; 4,670,595; 4,122,118; 4,614, 817; 4,209,463; 4,196,146; 4,187,249; 4,140,716. This method is disadvantageous in that the halide that is displaced is corrosive to the reactors and appears in the waste stream and must therefore be disposed of at considerable expense. Furthermore, use of an aniline derivative such as formanilide, and use of p-chloro-nitrobenzene, requires additional manufacturing equipment and capabilities to produce such starting materials from aniline and nitrobenzene, respectively.

It is also known to prepare 4-ADPA from the head-to-tail coupling of aniline. See, for example, G.B. 1,440,767 and U.S. Pat. No. 4,760,186. This method is disadvantageous in that the yield of 4-ADPA is not acceptable for a commercial process. It is also known to decarboxylate a urethane to produce 4-NDPA. See U.S. Pat. No. 3,847,990. However, such method is not commercially practical in terms of cost and yield.

It is known to prepare 4-ADPA by hydrogenating p-nitrosodiphenylhydroxylamine which can be prepared by catalytic dimerization of nitrosobenzene utilizing, as a reducing agent, aliphatic compounds, benzene, naphthalene or ethylenically unsaturated compounds. See, for example, U.S. Pat. Nos. 4,178,315 and 4,404,401. It is also known to prepare p-nitrosodiphenylamine from diphenylamine and an alkyl nitrate in the presence of excess hydrogen chloride. See, for example, U.S. Pat. Nos. 4,518,803 and 4,479,008.

It is also known to produce 4-nitrosodiphenylamine by reacting acetanilide and nitrobenzene in DMSO in the presence of sodium hydroxide and potassium carbonate at 80° C. for 5 hours. See Ayyangar et al., Tetrahedron Letters, Vol. 31, No. 22, pp. 3217–3220 (1990). See also, Wohl, Chemische Berichte, 36, p. 4135 (1903) and Chemische Berichte, 34, p. 2442 (1901). However, the yield of 4-nitrosodiphenylamine is low and is therefore not commercially practical. Furthermore, such method requires utilization of an aniline derivative, namely, acetanilide, and therefore increases the cost of the starting materials.

It is known to prepare 4-ADPA by the successive steps of a) reacting aniline with nitrobenzene in the presence of a base, under controlled conditions to produce a mixture containing the salts of 4-nitrodiphenylamine and of 4-nitrosodiphenylamine and then b) hydrogenating the salts. U.S. Pat. No. 5,117,063 discloses such a process.

U.S. Pat. No. 5,420,354, shows another process for the preparation of p-aminodiphenylamine by contacting nitrobenzene with hydrogen and aniline in the presence of a hydrogenation catalyst, a hydrogenation inhibitor and an acid catalyst. While this latter process is described as a one-step process, selectivity to the desired product is relatively low.

The process of the present invention produces 4-ADPA in a one-step process, wherein Ynitrobenzene is charged to a reactor zone under hydrogen pressure in the presence of a strong organic base and a catalyst for hydrogenation. The various reactions take place in the same reactor, preferably over a fixed bed, to produce 4-ADPA in one continuous processing step. In addition, the process of the present invention is much less expensive in terms of manufacturing costs, as well as the cost of raw materials, due to the convenience of a one-step process. Finally, this process produces improved yields and selectivities.

SUMMARY OF THE INVENTION

This invention provides a method for preparing 4-ADPA by charging nitrobenzene into a reaction zone under hydrogen pressure in the presence of a strong organic base and a catalyst for hydrogenation. The method provides the convenience and economy of a one-step process, while producing improved yields and selectivities.

There is further provided a method whereby the 4-ADPA produced under hydrogen pressure in the process just mentioned is further hydrogenated to produce alkylated paraphenylenediamine (PPD) antidegradants and/or antiozonants for polymers, most particularly for rubber.

Yet another method of this invention is the process by which the 4-ADPA is reductively alkylated to produce alkylated PPD.

More particularly, the present invention is directed to a method of preparing 4-ADPA, an intermediate to PPD, wherein nitrobenzene in the presence of a strong organic base is charged to a reaction zone under hydrogen pressure. A hydrogenation catalyst is charged to the reaction zone at the start of the reaction, as opposed to the method set forth in U.S. Pat. No. 5,453,541, owned by our common assignee and incorporated herein by reference. With this new inventive method, the reaction is a one-step process wherein nitrobenzene is converted to aniline and the head-to-tail coupling of aniline and nitrobenzene is initiated in the presence of a strong organic base. The resulting reactions produce a mixture rich in 4-ADPA intermediates, or the substituted derivatives thereof, including the 4-nitrodiphenylamine and/or 4-nitrosodiphenylamine salts, and then 4-ADPA as the hydrogenation product thereof. A key to the current process obtaining high yield and selectivity to 4-ADPA is manipulation of the reaction to produce more aniline. Otherwise, the yield of nitrobenzene is lost to azoxybenzene, and another reaction step is required to recover aniline from the azoxybenzene product, as in the catalytic hydrogenation of azoxybenzene. In this current inventive process, the resulting 4-ADPA can be utilized to prepare alkylated products of p-phenylenediamine, which products are useful as antioxidants and antiozonants. Alternatively, the 4-ADPA intermediates can be reduced and the reduced material alkylated in the same reaction vessel utilizing a ketone as a solvent.

In one embodiment of the invention, particular attention is paid to the molar ratio of nitrobenzene to tetramethylammonium hydroxide (TMA(OH)). In that instance where this ratio is maintained at a level less than 1.0, the selectivity of the hydrogenation reaction whereby nitrobenzene is hydrogenated in a one-step process, under hydrogen pressure and in the presence of a strong organic base, i.e., TMA(OH), and a hydrogenation catalyst, to 4-ADPA is enhanced.

In another embodiment of the invention, the one-step hydrogenation of nitrobenzene to 4-ADPA, in the presence of a strong organic base and a hydrogenation catalyst, under hydrogen pressure, is enhanced by the use of a noble metal catalyst on an appropriate support, preferably palladium or platinum, most preferably palladium on a carbon or alumina support. In yet another embodiment of the invention, the level of palladium employed is controlled to optimize the yield and selectivity to 4-ADPA.

In still another embodiment of the invention, the molar ratio of aniline to nitrobenzene is controlled such that yield and selectivity to 4-ADPA are optimized for the one-step conversion process whereby nitrobenzene undergoes hydrogenation, under hydrogen pressure and in the presence of a strong organic base and a hydrogenation catalyst, to 4-ADPA. Alternatively, aniline, though generated during the hydrogenation process, may additionally be charged to the reactor in order to achieve the desired aniline/nitrobenzene molar ratio.

DETAILED DESCRIPTION OF THE INVENTION

Statement of the Invention

The subject method for producing 4-ADPA comprises charging nitrobenzene to a confined zone under hydrogen pressure, and in the presence of a suitable base and a hydrogenation catalyst, and hydrogenating the nitrobenzene to produce 4-aminodiphenylamine (4-ADPA).

More particularly, the subject invention involves charging nitrobenzene to a confined zone, or a reactor or reaction zone, under hydrogen pressure and in the presence of a strong organic base and a catalyst for hydrogenation. As the nitrobenzene is hydrogenated it generates aniline in situ, which reacts with a portion of the nitrobenzene to produce 4-ADPA intermediates, specifically salts of 4-nitrodiphenylamine (4-NDPA) and 4-nitrosodiphenylamine (4-NODPA), among other reaction products. The hydrogenation reaction further converts these 4-NDPA and 4-NODPA intermediates to 4-ADPA as the reaction proceeds. One advantage of the foregoing process is the capability to achieve 4-ADPA in a one-step, or one-pot, reaction process. A key to obtaining high yield and selectivity to 4-aminodiphenylamine is to push the reaction to make more aniline; otherwise, the yield of nitrobenzene is lost to azoxybenzene or another step will be required to recover aniline from azoxybenzene as in the catalytic hydrogenation of azoxybenzene.

Alternatively, for producing 4-ADPA it is possible to enhance the intermediate (4-NDPA and 4-NODPA) generation by introducing a separate charge of aniline to the reaction zone simultaneously with the nitrobenzene.

For producing alkylated PPD, of which 4-ADPA is an intermediate, the subject method includes the further step of hydrogenating the 4-ADPA to effect conversion to alkylated PPD, an antidegradant/antizonant for polymers, particularly rubber. Further, for producing alkylated p-phenylenediamines the subject method includes the step of reductively alkylating the 4-ADPA produced above to obtain the alkylated PPD.

Several factors are identified as having a benefit in optimization of the one-step process provided herein for the conversion of nitrobenzene to 4-ADPA. One such factor involves control of the molar ratio of nitrobenzene to the TMA(OH) base material. This ratio should be no greater than 1.0 and preferably less than 1.0. At a nitrobenzene:TMA(OH) molar ratio greater than 1.0, the hydrogenation reaction to produce 4-ADPA is unfavorably affected in that the selectivity shifts to formation of azoxybenzene, aniline and diphenylhydrazine rather than selectivity to 4-aminodiphenylamine.

Another parameter of the one-step process of the invention is grounded in the choice of hydrogenation catalyst, and the amount of catalyst and the level of the catalyst on the support.

Yet one more factor which can be controlled to affect optimization of 4-ADPA yield and selectivity is the molar ratio of aniline to nitrobenzene available in the reaction zone. The molar ratio of aniline to nitrobenzene can vary from a large excess of nitrobenzene to a large excess of aniline. Preferably, the reaction is conducted utilizing an excess of aniline. The ratio of 4-NDPA to 4-NODPA produced in the reaction of the present invention can be controlled by varying the ratio of aniline to nitrobenzene. For example, the higher the ratio of aniline to nitrobenzene, the higher the ratio of 4-NODPA to 4-NDPA. Preferable in this one-step process is the charging of nitrobenzene, and aniline if charged, to achieve a molar ratio of aniline to nitrobenzene of 4 to 1. This is preferable because control of selectivity to higher 4-ADPA can be easily achieved. However, with excess amounts of nitrobenzene, given the proper level of hydrogenation catalyst, some amount of nitrobenzene will be lost to nitrobenzene reduction products, i.e., azoxybenzene, azobenzene, and diphenylhydrazine.

In addition to the foregoing factors, essential to the one-step process is conducting the process under hydrogen pressure. The hydrogen pressure in the reaction zone mentioned herein provides a driving force to effect hydrogenation during the method of the invention. For very active hydrogenation catalysts, such as those classified as noble metals, the gauge pressure is preferably between 0 and 7000 kPa under either hydrogen flow control or pressure control. The rate of hydrogen uptake during flow control is equally important in affecting the selectivity to 4-nitrosodiphenylamine, and eventually to 4-aminodiphenylamine. The flow rate used will be dependent upon the type and level of catalyst.

For example, an active hydrogenation catalyst such as palladium on carbon at higher levels will have larger hydrogen uptake which consequently promotes the reduction of nitrobenzene to unwanted by-products such as azoxybenzene, which lowers the selectivity to 4-ADPA. In such a catalytic system, the flow can be regulated to lower pressures (such as those lower than 700 kPa) and higher levels of tetramethylammonium hydroxide, TMA(OH), which consequently increase the yield of nitrobenzene to 4-ADPA.

Another aspect of this invention is the use of a base material, in the presence of which the nitrobenzene charge is hydrogenated. Suitable bases include, but are not limited to, inorganic bases such as, for example, alkali metals, such as sodium metal, alkali metal hydrides, hydroxides and alkoxides, such as sodium hydride, lithium hydroxide, sodium hydroxide, cesium hydroxide, potassium hydroxide, potassium t-butoxide, and the like, including mixtures thereof. Preferred are strong organic bases, such as alkali metal alkoxides such as sodium or potassium alkoxide. Other acceptable base materials include, but are not limited to, phase transfer catalysts in conjunction with a suitable base source such as tetrasubstituted ammonium hydroxides wherein each substituent is independently selected from alkyl, aryl or arylalkyl groups, including tetraalkylammonium hydroxides, e.g., tetramethylammonium hydroxide, aryl, trialkyl ammonium hydroxides, e.g., phenyltrimethylammonium hydroxide, arylalkyl, trialkylammonium hydroxides, e.g., benzyl trimethylammonium hydroxide, alkyl substituted diammonium hydroxides, e.g., bisdibutylethyl hexamethylene diammonium hydroxide, and other combinations of phase transfer catalysts and suitable bases such as suitable bases in conjunction with aryl ammonium salts, crown ethers and the like, and amine bases, such as lithium bis(trimethylsilyl) amide, and the like, including mixtures thereof. Preferred materials for use as bases are tetraalkylammonium hydroxides such as tetramethylammonium hydroxide (TMA(OH)). The amount of base utilized in the present process can vary over a wide range and is dependent, for example, on, among other factors, the degree to which a specific reaction product is desired to be enhanced or minimized. For example, the reaction can be conducted in a manner which is limiting in base or the reaction can be conducted in a manner which is limiting in nitrobenzene or aniline. As was mentioned earlier, the base should be used in an amount sufficient to achieve a molar ratio of nitrobenzene to TMA(OH) of less than one (1.0). For a semibatch mode, for example, the base is added to the reaction zone either above or below the reaction zone surface. In this instance, the base preferably is in the hydrate form, such as the dihydrate.

Also included in the process of the invention is the use of a hydrogenation catalyst. Hydrogenation catalysts are well known in the art. There is a variety of catalyst types that are appropriate as reduction catalysts for the present invention. Among these are the following, and others of similar nature: copper on alumina or pumice; silver-magnesium oxide on pumice; copper-cerium oxide on pumice; copper-manganese oxide or iron-manganese oxide on pumice; copper on silica; platinum on activated carbon or carbon black; nickel on silica or kieselguhr; molybdenum or palladium on carbon or alumina using catalyst inhibitors such as thiophene, thiourea, triphenyl phosphite, polyamines, magnesium oxide, morpholine, and thioethers; and sulfided noble metal catalysts using sulfiding agents such as hydrogen sulfide, sodium sulfide, ammonium sulfide, and dimethyl sulfoxide. The choice of catalyst should be that which retards or inhibits the direct hydrogenation of nitrobenzene to a terminal product, such as azoxybenzene, and instead allows the head-to-tail coupling of aniline and nitrobenzene. For example, using copper chromite would restrict the hydrogenation of nitrobenzene to azoxybenzene, and will initially increase the rate of head-to-tail coupling of aniline and nitrobenzene to the 4-NODPA and 4-NDPA salt which will, at the right pressure, hydrogenate directly to 4-ADPA.

The invention, as described hereinabove, allows for the production of 4-ADPA with only nitrobenzene, hydrogen, an organic base and an hydrogenation catalyst as starting materials. The reaction events, such as the head-to-tail coupling of aniline and nitrobenzene and the hydrogenation of the salts of 4-NODPA and 4-NDPA to 4-ADPA, are not separated. Also, given the proper choice of molar ratios of aniline to nitrobenzene and nitrobenzene to organic base, and the proper weight ratio of organic base to hydrogenation catalyst, optimal selectivity to 4-ADPA can be achieved without continuous removal of protic material, such as water. Protic material removal can, however, enhance selectivities in some reaction modes. These factors are advances over the invention of U.S. Pat. No. 5,453,541, referred to hereinabove. In the present invention, this protic removal is not necessary so long as the requirements are satisfied for increased selectivity to 4-ADPA, which includes choosing the proper aniline to nitrobenzene, nitrobenzene to organic base molar ratios and the weight ratios of organic base to the hydrogenation catalyst. In the present invention, the water removal can be effected to further improve the selectivity using a different reactor set up, such as a continuous fixed bed of hydrogenation catalyst where the water removal does not require vacuum conditions. Also, the production of 4-ADPA in the present invention requires elevated pressures without significant regard to the removal of the protic material, such as water.

In the method of the current invention, the nitrobenzene is preferably charged to the reaction zone gradually, over a period of time, usually over from 0.1 to 10 hours. The temperature in the reaction zone is preferably 90° C. and is held isothermally. The hydrogen gauge pressure at either flow or pressure control is 0 to about 3000 kPa. At constant hydrogen pressure, near the end of the process, the pressure is 2.757 kPa to 3.102 kPa.

As the nitrobenzene is charged over time, it initially undergoes head-to-tail coupling of aniline and nitrobenzene to produce the tetramethylammonium (TMA) salts of 4-nitrosodiphenylamine and 4-nitrodiphenylamine. Depending upon the ratio of aniline to nitrobenzene and the catalyst level, the following products are formed: azoxybenzene, axobenzene, diphenylhydrazine and 4-ADPA. For example, in the presence of a large excess of the nitrobenzene (molar ratio of aniline to nitrobenzene of much less than one, or close to zero), azoxybenzene is the major side product. On the other hand, in excess aniline (or when the molar ratio of aniline to nitrobenzene is much greater than one) the major by-products are diphenylhydrazine and azobenzene. The tetramethylammonium salts of 4-NODPA and 4-NDPA are catalytically reduced to yield 4-ADPA and tetramethylammonium hydroxide.

Preferably, in a semi-batch mode, nitrobenzene can be charged over time to achieve the highest possible selectivity to 4-ADPA. In this mode, the amount of organic base, such as TMA(OH), relative to nitrobenzene is larger, and with an appropriate amount of hydrogenation catalyst present, a higher selectivity to 4-ADPA can be obtained. The end point for the reaction is determined by the amount of water produced in the reduction reaction, because at high water content (on the order, for example, of 4% by volume) the head-to-tail coupling of aniline and nitrobenzene is diminished and the reaction shifts to favor the formation of azoxybenzene.

The selectivity to 4-ADPA can also be enhanced by manipulating the hydrogen flow control so that the head-to-tail coupling of aniline and nitrobenzene is effected against the direct hydrogenation of nitrobenzene to the terminal product, such as azoxybenzene. This hydrogenation flow rate is controlled so that the pressure is in the lower portion of the range.

Another alternative to semi-batch mode is a continuous process where a fixed bed of hydrogenation catalyst is fed continuously with aniline, nitrobenzene, hydrogen and the organic base, such as tetramethylammonium hydroxide pentahydrate that is predissolved in the aniline system. The value of the flow rates for these feed streams should correspond to those that will yield the maximum selectivity to 4-ADPA, i.e., the molar ratio of aniline to nitrobenzene is preferably 4 to 1 or greaterand the molar ratio of nitrobenzene to the organic base is preferably close to or less than 1. The amount of hydrogenation catalyst to be used is low at the entrance of the reactor and gradually increases to such an extent that the salts of 4-NODPA and 4-NDPA are converted to 4-ADPA. Furthermore, using this mode of operation, the continuous removal of water is facilitated, thereby promoting higher selectivity to 4-ADPA.

In the alternative batch mode, the nitrobenzene may be charged to the reaction zone all at once at such a proportion that the moles of nitrobenzene is about less than the mole of organic base. This mode of addition needs a specific amount of hydrogenation catalyst so that a portion of nitrobenzene is not lost to terminal products such as azoxybenzene. However, with aniline initially charged in the reaction zone, the gradual addition of nitrobenzene is preferable for higher 4-ADPA selectivity.

The reaction zone is preferably maintained at a temperature between 20° C. and 200° C., more preferably from 80° C. to 100° C.

While nitrobenzene and aniline (if used) are recited as reactants, the method is also applicable to the use of nitrobenzene or aniline compounds containing one or more nuclear substituents which do not interfere with the reaction.

A diluent or solvent may be employed in the method of the invention, provided that it does not interfere with the reactions involved. Suitable solvent systems include, but are not limited to, solvents such as, for example, dimethylsulfoxide, N-methylpyrrolidone, dimethylformamide, aniline, pyridine, nitrobenzene, nonpolar hydrocarbon solvents such as toluene and hexane, ethyleneglycol dimethyl ether, diisopropyl ethylamine, and the like, as well as mixtures thereof. Also, an amount of aniline in excess of that needed for the reaction may be charged to the reaction zone, in which case this excess of aniline serves as the solvent.

As used herein, the term "substituted aniline derivatives" means aniline containing one or more electron withdrawing or electron releasing substituents on the aromatic ring. Applicable substituents include, but are not limited to, halides, —$NO_2$, —$NH_2$, alkyl groups, alkoxy groups, —$SO_3$, —COOH and aryl, aralkyl or alkaryl groups containing at least one —$NH_2$ group. Halides are selected from the group consisting of chloride, bromide and fluoride. The preferred alkyl and alkoxy groups contain from 1 to about 6 carbon atoms. The preferred aryl, aralkyl and alkaryl groups contain from about 6 to about 18 carbon atoms. Examples of substituted aniline derivatives include, but are not limited to, 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline, 1,3,5-triaminobenzene and mixtures thereof.

Azobenzene is also produced in this reaction in variable quantities depending on the reaction conditions. Azobenzene is an undesirable product, however, because it represents a loss in yield and selectivity to 4-ADPA. One way of controlling azobenzene production is through the ratio of aniline to nitrobenzene. Thus, as this ratio is increased, the amount of azobenzene generally decreases. As discussed below, and as illustrated in the Examples set forth below, other variables, such as the amount of base and oxygen, can also affect the amount of azobenzene produced. Thus, utilizing the teachings of the present invention, one skilled in the art can conduct the reaction of the present invention to control the amount of azobenzene that is produced.

The reaction comprising the one-step process is conducted at a suitable temperature which can vary over a wide range. For example, the temperature can fall within a range of from about 80° C. to about 150° C., such as from about 80° C. to about 100° C., preferably from about 80° C. to about 90° C. A most preferred temperature for conducting the reaction of the present invention is from about 80° C. to about 90° C., such as at 85° C.

Control of the amount of water generated during the reaction process is important. Water is generated by the reduction of nitrobenzene to azoxybenzene, by the head-to-tail coupling of aniline and nitrobenzene to their corresponding 4-NODPA and 4-NDPA salts, and by the reduction of 4-NDPA salt to 4-ADPA. Water in the reaction zone inhibits the reaction of the aniline with the nitrobenzene to an extent where the reaction is no longer significant, i.e., 4-ADPA yield is less than desired. Controlling the reaction so that the amount of water generated to below about the 4% level causes the reaction to proceed in an acceptable manner. In a preferred embodiment, when tetramethylammonium hydroxide is utilized as a base, and with aniline as a solvent, as the amount of water is reduced further, e.g., down to about 0.5% based of the volume of the reaction mixture, the total amount of 4-NDPA and 4-NODPA and/or salts thereof increases. Thus, the present reaction could be conducted under anhydrous conditions. A "controlled amount" of water generated is an amount up to that which inhibits the reaction of aniline with nitrobenzene, e.g., up to about 4% $H_2O$ based on the volume of the reaction mixture when aniline is utilized as the solvent. The upper limit for the amount of water acceptable in the reaction varies with the solvent. For example, when DMSO is utilized as the solvent and tetramethylammonium hydroxide is utilized as the base, the upper limit on the amount of water generated in the reaction is about 8% $H_2O$ based on the volume of the reaction mixture. However when aniline is utilized as a solvent with the same base, the upper limit is 4% $H_2O$ based on the volume of the reaction mixture. In addition, the amount of generated water tolerated will vary with type of base, amount of base, and base cation, used in the various solvent systems. However, it is within the skill of one in the art, utilizing the teachings of the present invention, to determine the specific upper limit of the amount of generated water for a specific solvent, type and amount of base, base cation and the like. The minimum amount necessary to maintain selectivity of the desired products will also depend on the solvent, type and amount of base, base cation and the like, that is utilized and can also be determined by one skilled in the art.

In one embodiment, the amount of generated water present in the reaction zone of the process is controlled by continuously removing the generated water using a continuous flow fixed bed-type reactor as described above. The continuous removal of generated water will increase the formation of the salts of 4-NODPA and 4-NDPA, and thereby increases the selectivity to 4-ADPA.

Reductive alkylation of 4-ADPA to produce antiozonants can be conducted by any one of several well known methods. See, for example, U.S. Pat. No. 4,900,868. Preferably, 4-ADPA and a suitable ketone or aldehyde are reacted in the presence of hydrogen and platinum-on-carbon as catalyst. Suitable ketones include methylisobutyl ketone (MIBK), acetone, methylisoamylketone and 2-octanone. It should be noted that reduction of the 4-ADPA intermediates and alkylation of the reduced material can be conducted in the same reaction vessel utilizing the ketone as a solvent. See, for example, U.S. Pat. No. 4,463,191, and Banerjee et al, J. Chem. Soc. Chem. Comm. 18, 1275–76 (1988).

Contemplated equivalents of the reactants and reagents set forth above are reactants and reagents otherwise corresponding thereto and having the same general properties wherein one or more of the various groups, e.g., $NO_2$, are simple variations. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the method of this invention. Occasionally, the reaction conditions may not be applicable as specifically described to each reactant and reagent within the disclosed scope. For example, certain suitable bases may not be as soluble in one solvent as they are in other solvents. The reactants and reagents for which this occurs will be readily recognized by those skilled in the art. In all such cases, either the reactions can be successfully performed by conventional modifications known to those skilled in the art, e.g., by appropriate adjustments in temperature, pressure and the like, by changing to alternative conventional reagents such as other solvents or other bases, by routine modification of reaction conditions, and the like, or other reactions disclosed herein or otherwise conventional, will be applicable to the method of this invention. In all preparative methods, all starting materials are known or are readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received, unless otherwise stated, and all yields were determined by HPLC as recited.

The method of the invention may be completely understood by reference to the following examples, in which all temperatures are in degrees Celsius, all pressures are gauge pressures and all proportions are by weight unless otherwise stated. 4-NDPA and 4-NODPA are present as their salts.

EXAMPLE 1

Into a 300 ml Parr autoclave were charged 133.3 gm nitrobenzene, 26.1 gm TMA(OH). $5H_2O$ and 0.742 gm hydrogenation catalyst (5% palladium on an alumina carrier). Hydrogen was fed under control to the autoclave for a period of three hours, during which the pressure rose from 400 kPa at peak flow (10 l/hr at 70° F. and 1 atm.) and 73° C. The contents of the autoclave were then raised to 87° C., and a hydrogen pressure of 2900 kPa for a period of 2.5 hours.

Using known HPLC techniques, the composition in the autoclave was determined, first at one (1) hour, and again at five and a half (5.5) hours. The following is a summary of the reaction zone composition.

TABLE I

| Time Component | 1 hour Weight % | 5.5 hours Weight % |
|---|---|---|
| aniline | 0.215 | 3.665 |
| n-methylaniline | 0.0 | 0.0 |
| nitrobenzene | 79.421 | 10.195 |
| 4-aminodiphenylamine (4-ADPA) | 0.899 | 0.603 |
| phenazine | 0.0 | 0.01 |

TABLE I-continued

| Time Component | 1 hour Weight % | 5.5 hours Weight % |
|---|---|---|
| 2-aminodiphenylamine (2-ADPA) | 0.074 | 0.0 |
| 4-nitrosodiphenylamine (4-NODPA) | 0.118 | 0.047 |
| c-azobenzene | 0.0 | 0.073 |
| diphenylhydrazine | 0.0 | 0.0 |
| 4-nitrodiphenylamine (4-NDPA) | 0.022 | 0.1 |
| azoxybenzene | 19.152 | 82.960 |
| 2-nitrodiphenylamine (2-NDPA) | 0.0 | 0.0 |
| t-azobenzene | 0.099 | 2.089 |
| 4-phenylazodiphenylamine (4-PADPA) | 0.0 | 0.057 |

The data in Table I indicates that a perceptible, though small amount of 4-ADPA, the desired product, is formed.

EXAMPLE 2

This example explores the effect of the additional presence of aniline initially. The same technique used in Example 1 was employed, except that 136.9 gm aniline and 43.7 gm nitrobenzene were initially charged, along with 58.0 gm TMA(OH).$5H_2O$ and 1.05 gm of the hydrogenation catalyst. Thus, the reactor was initially charged with aniline at a 4.165 mole ratio of aniline to nitrobenzene. Using HPLC techniques, the composition in the autoclave was determined, first at 1.11 hours, then at 3.6 hours, and finally at 5.61 hours. Reactor temperature was controlled at about 94° C. throughout the duration of the reaction. At 3.46 hours, an amount of water had been formed which was sufficient to cause the formation of two phases, a heavier organic phase and a lighter aqueous phase. Through the rest of the reaction process the large amount of water inhibits formation of anilide ion, which is a precursor to the coupling of aniline and nitrobenzene to form 4-APDA.

TABLE IIA

Nitrobenzene Hydrogenation: Example 2
Product Distribution in Weight Percent -
Organic Layer

| Time Component | 1.11 hours Weight % | 3.46 hours Weight % | 5.61 hours Weight % |
|---|---|---|---|
| aniline | 66.64 | 57.65 | 56.999 |
| n-methylaniline | 0.0 | 0.0 | 0.0 |
| nitrobenzene | 7.195 | 0.0 | 0.0 |
| 4-aminodiphenylamine (4-ADPA) | 0.55 | 15.41 | 14.95 |
| phenazine | 0.126 | 0.126 | 0.108 |
| 2-aminodiphenylamine (2-ADPA) | 0.0 | 0.0 | 0.0 |
| 4-nitrosodiphenylamine (4-NODPA) | 11.457 | 0.034 | 0.0322 |
| c-azobenzene | 2.46 | 2.44 | 1.266 |
| diphenylhydrazine | 0.0 | 19.56 | 23.379 |
| 4-nitrodiphenylamine (4-NDPA) | 2.738 | 0.1305 | 0.0 |
| azoxybenzene | 2.194 | 0.0435 | 0.0 |
| 2-nitrodiphenylamine (2-NDPA) | 0.0 | 0.032 | 0.035 |

TABLE IIA-continued

Nitrobenzene Hydrogenation: Example 2
Product Distribution in Weight Percent -
Organic Layer

| Time<br>Component | 1.11 hours<br>Weight % | 3.46 hours<br>Weight % | 5.61 hours<br>Weight % |
|---|---|---|---|
| t-azobenzene | 6.168 | 4.346 | 3.181 |
| 4-phenylazodiphenylamine (4-PADPA) | 0.216 | 0.0214 | 0.0 |

TABLE IIB

Nitrobenzene Hydrogenation: Example 2
Product Distribution in Weight Percent
for Composite and Water Layers

| | Time | |
|---|---|---|
| Component | 3.46 hours<br>Weight %<br>composite | 5.61 hours<br>Weight %<br>water layer |
| aniline | 60.58 | 67.321 |
| n-methylaniline | 0.0 | 0.0 |
| nitrobenzene | 0.044 | 0.196 |
| 4-aminodiphenylamine (4-ADPA) | 15.357 | 12.451 |
| phenazine | 0.130 | 0.743 |
| 2-aminodiphenylamine (2-ADPA) | 0.0 | 0.0 |
| 4-nitrosodiphenylamine (4-NODPA) | 0.0444 | 0.0 |
| c-azobenzene | 2.537 | 3.164 |
| diphenylhydrazine | 13.798 | 7.948 |
| 4-nitrodiphenylamine (4-NDPA) | 0.141 | 0.0 |
| azoxybenzene | 0.066 | 0.0 |
| 2-nitrodiphenylamine (2-NDPA) | 0.032 | 0.044 |
| t-azobenzene | 6.605 | 8.134 |
| 4-phenylazodiphenylamine (4-PADPA) | 0.018 | 0.0 |

In contrast to Example 1, Example 2 clearly demonstrates that in the presence of excess aniline, i.e., mole aniline/mole nitrobenzene greater than 1, the hydrogenation of nitrobenzene favors the formation of the TMA salts of 4-NODPA and 4-NDPA, as well as the total conversion of nitrobenzene, thus enhancing 4-ADPA yield and selectivity. As shown in Table IIA and IIB, nitrobenzene conversion is near 100% at 3.46 hours, and the hydrogenation reaction is essentially complete. The remaining reaction time, from 3.46 to 5.61 hours, was used as a finishing up of the reduction of the azobenzene byproduct to diphenylhydrazine and the reductive disproportionation of 4-phenylazo DPA to 4-ADPA and aniline.

EXAMPLE 3

In Example 3, the mole ratio of aniline to nitrobenzene was raised to 7.07, or 1.7 times that shown in Example 2. The amount of 5% palladium catalyst on alumina was about equal to that used in Example 2. In this Example, however, the amount of base relative to nitrobenzene was slightly smaller than Example 2. Concomitantly, the amount of nitrobenzene per unit weight of catalyst was lower in Example 3 than as shown in Example 2. Once again, the reaction mass was transformed from a single phase at the outset to two liquid phases, a heavy organic phase and a lighter aqueous phase. The reaction time at 6 hours represented the end of hydrogenation which was preceded by constant pressure hydrogenation. The selectivity results shown in Table IIIA and Table IIIB closely resemble those of Example 2, Table IIA and Table IIB, with the exception that a relatively lower conversion of nitrobenzene to coupling reaction products is seen.

TABLE IIIA

Nitrobenzene Hydrogenation: Example 3
Product Distribution in Weight Percent of Composite

| Time<br>Component | 1.45 hours<br>Weight % | 2.79 hours<br>Weight % | 6.0 hours<br>Weight % |
|---|---|---|---|
| aniline | 78.16 | 72.33 | 74.69 |
| n-methylaniline | 0.0 | 0.0 | 0.0 |
| nitrobenzene | 0.0 | 0.0 | 0.0 |
| 4-aminodiphenylamine (4-ADPA) | 8.446 | 7.91 | 8.35 |
| phenazine | 0.067 | 0.0623 | 0.06 |
| 2-aminodiphenylamine (2-ADPA) | 0.025 | 0.0 | 0.0255 |
| 4-nitrosodiphenylamine (4-NODPA) | 1.246 | 0.449 | 0.528 |
| c-azobenzene | 0.0 | 0.0 | 0.0 |
| diphenylhydrazine | 6.012 | 17.19 | 12.136 |
| 4-nitrodiphenylamine (4-NDPA) | 0.0 | 0.0 | 0.0 |
| azoxybenzene | 0.0 | 0.0 | 0.0 |
| 2-nitrodiphenylamine (2-NDPA) | 0.0 | 0.059 | 0.036 |
| t-azobenzene | 5.977 | 1.996 | 4.169 |
| 4-phenylazodiphenylamine (4-PADPA) | 0.067 | 0.0 | 0.0 |

TABLE IIIB

Nitrobenzene Hydrogenation: Example 3
Product Distribution in Weight Percent
for Organic and Water Layers at End of Reaction

| Time<br>Component | 6.0 hours<br>Organic Layer | 6.0 hours<br>Water Layer |
|---|---|---|
| aniline | 72.0 | 81.62 |
| n-methylaniline | 0.0 | 0.0 |
| nitrobenzene | 0.0 | 0.0805 |
| 4-aminodiphenylamine (4-ADPA) | 8.32 | 7.441 |
| phenazine | 0.06 | 0.0594 |
| 2-aminodiphenylamine (2-ADPA) | 0.024 | 0.0 |
| 4-nitrosodiphenylamine (4-NODPA) | 0.279 | 0.691 |
| c-azobenzene | 0.0 | 0.0 |
| diphenylhydrazine | 16.227 | 3.413 |
| 4-nitrodiphenylamine (4-NDPA) | 0.0 | 0.0 |
| azoxybenzene | 0.0 | 0.0 |
| 2-nitrodiphenylamine (2-NDPA) | 0.0355 | 0.0279 |
| t-azobenzene | 2.86 | 6.667 |
| 4-phenylazodiphenylamine (4-PADPA) | 0.0 | 0.0 |

Example 3 demonstrates a lower nitrobenzene conversion to 4-NDPA and 4-NODPA due to a lower amount of base and a higher amount of palladium catalyst, which caused the hydrogenation of nitrobenzene to diphenylhydrazine to generate large amounts of water. The large amount of palladium catalyst used per gram of nitrobenzene indicates a larger turnover number for the reduction of nitrobenzene and therefore the rate of nitrobenzene conversion is higher in Example 3 than in Example 2.

As in Example 2, the inhibitory effect of water on the production of anilide ions limited the direct conversion of nitrobenzene to the coupling reaction products. The high mole ratio of aniline to nitrobenzene and the higher palladium to nitrobenzene ratio yields 4-NODPA exclusively. As is seen in Table IIIA, after 1.45 hours of reaction time, no 4-NDPA was detected.

Table IV exhibits comparatively the mole ratio values and amounts of the various reaction/reactor components and products for Example 1, 2 and 3.

TABLE IV

Nitrobenzene Hydrogenation: Reactor Examples

| Example No. | 1 | 2 | 3 |
|---|---|---|---|
| gm aniline | 0.0 | 136.9322 | 160.2318 |
| gm nitrobenzene | 133.3214 | 43.6787 | 30.1102 |
| mole aniline/ mole nitrobenzene | 0.0 | 4.165 | 7.07 |
| gm-TMA(OH).5H$_2$O | 26.1044 | 58.0247 | 39.7038 |
| mole nitrobenzene/ mole TMA(OH) | 7.453 | 1.099 | 1.11 |
| gm 5% Pd/Al$_2$O$_3$ | 0.7421 | 1.0475 | 1.0480 |
| gm Pd/1000 gm nitrobenzene | 0.278 | 1.208 | 1.76 |

The foregoing Examples would suggest that significant yields of conversion of nitrobenzene to 4-ADPA may be obtained using excess tetramethylammonium hydroxide, i.e., mole nitrobenzene/mole TMA(OH) less than 1, and an appropriate amount of palladium catalyst. The foregoing is best accomplished by using a continuous feeding of nitrobenzene at a rate that meets the requirement of excess base and the generation of a small amount of water so as not to inhibit the anilide ion generation.

The results from Examples 2 and 3 show that the overall rate of consumption of nitrobenzene to coupling reaction products (and hence an appreciable rate of formation of anilide ion) is governed by the relative amounts of catalyst and TMA(OH). Given the foregoing results, a large amount of palladium catalyst is not recommended.

I claim:

1. A one-step process for preparing 4-ADPA comprising charging nitrobenzene into a reaction zone under hydrogen pressure and in the presence of a base material and a hydrogenation catalyst said catalyst being charged to the reaction zone at the start of the reaction.

2. The process of claim 1 wherein said 4-ADPA is further hydrogenated to produce alkylated paraphenylenediamine.

3. The process of claim 1 wherein the 4-ADPA is further reductively alkylated to produce alkylated paraphenylenediamine.

4. The process of claim 1 wherein the base material is selected from 1–6 carbon alkoxides and quaternary amine hydroxides.

5. The process of claim 1 wherein the base material is selected from the group consisting of inorganic bases selected from the group consisting of alkali metals, alkali metal hydrides, alkali metal hydroxides, and alkali metal alkoxides, including mixtures thereof, and organic bases selected from the group consisting of strong alkali metal alkoxide bases, and other base materials selected from phase transfer catalysts in conjunction with a base source including tetrasubstituted ammonium hydroxides wherein each substituent is independently selected from alkyl, aryl, or arylalkyl groups, aryl trialkylammonium hydroxides, arylalkyl trialkylammonium hydroxides, alkylsubstituted diammonium hydroxides, base materials in conjunction with aryl ammonium salts, crown ethers, and amine bases.

6. The process of claim 5 wherein the base material is a strong organic base and is tetramethylammonium hydroxide.

7. The process of claim 6 wherein the molar ratio of nitrobenzene to tetramethylammonium hydroxide is less than about 1.0.

8. The process of claim 1 wherein aniline is charged to the reaction zone such that said process is carried out in an excess of aniline.

9. The process of claim 8 wherein the molar ratio of aniline to nitrobenzene is about 4 to 1.

10. The process of claim 1 wherein the hydrogenation catalyst is a catalyst that promotes the head-to-tail coupling of aniline and nitrobenzene.

11. The process of claim 10 wherein the hydrogenation catalyst comprises at least one of copper, silver-magnesium oxide, copper-cerium oxide, copper-manganese oxide, iron-manganese oxide, platinum, nickel, molybdenum, palladium, and sulfided noble metals, said metal being present on a suitable support selected from the group consisting of alumina, pumice, silica, activated carbon, and carbon black.

12. A process for the hydrogenation of nitrobenzene to 4-ADPA comprising: (a) preparing a reaction zone by supplying a strong organic base and a hydrogenation catalyst; (b) applying a flow of hydrogen at a pressure sufficient to force the conversion of nitrobenzene to 4-ADPA intermediates and to further hydrogenate the intermediates to 4-ADPA; (c) charging to the reaction zone an amount of nitrobenzene such that the molar ratio of aniline to nitrobenzene in the reaction zone is about 4.0 to 1.0, and that the molar ratio of nitrobenzene to the strong organic base is not greater than about 1.0; and (d) conducting the hydrogenation reaction for the conversion of nitrobenzene to 4-ADPA as a one-step process said catalyst being charged to the reaction zone at the start of the reaction.

13. The process of claim 12 wherein the nitrobenzene is charged to the reaction zone on a continuous basis.

14. The process of claim 12 wherein said 4-ADPA is further hydrogenated to produce alkylated paraphenylenediamine.

15. The process of claim 12 wherein the 4-ADPA is further reductively alkylated to produce alkylated paraphenylenediamine.

16. The process of claim 12 wherein the base material is selected from 1–6 carbon alkoxides and quaternary amine hydroxides.

17. The process of claim 12 wherein the base material is selected from the group consisting of inorganic bases selected from the group consisting of alkali metals, alkali metal hydrides, alkali metal hydroxides, and alkali metal alkoxides, including mixtures thereof, and organic bases selected from the group consisting of strong alkali metal alkoxide bases, and other base materials selected from phase transfer catalysts in conjunction with a base source including tetrasubstituted ammonium hydroxides wherein each substituent is independently selected from alkyl, aryl, or arylalkyl groups, aryl trialkylammonium hydroxides, arylalkyl trialkylammonium hydroxides, alkylsubstituted diammonium hydroxides, base materials in conjunction with aryl ammonium salts, crown ethers, and amine bases.

18. The process of claim 17 wherein the base material is a strong organic base and is tetramethylammonium hydroxide.

19. The process of claim 12 wherein aniline is charged to the reaction zone such that said process is carried out in an excess of aniline.

20. The process of claim 12 wherein the hydrogenation catalyst is a catalyst that promotes the head-to-tail coupling of aniline and nitrobenzene.

21. The process of claim 20 wherein the hydrogenation catalyst comprises at least one of copper, silver-magnesium oxide, copper-cerium oxide, copper-manganese oxide, iron-manganese oxide, platinum, nickel, molybdenum, palladium, and sulfided noble metals, said metal being present on a suitable support selected from the group consisting of alumina, pumice, silica, activated carbon, and carbon black.

22. The process of claim 12 wherein a controlled amount of water, up to that amount which inhibits the reaction of aniline with nitrobenzene, is generated during the hydrogenation reaction of nitrobenzene to 4-ADPA.

23. The process of claim 12 wherein the process is carried out as a continuous process and a fixed bed of hydrogenation catalyst is fed continuously with a charge of excess aniline, nitrobenzene, hydrogen and the strong organic base.

24. The process of claim 12 wherein the process is carried out in a semi-batch mode and nitrobenzene is charged to the reaction zone gradually over a period of time sufficient to achieve high selectivity to 4-ADPA and a charge of aniline is charged to the reaction zone initially with the nitrobenzene.

25. The process of claim 12 wherein the process is carried out in the batch mode and the entire charge of nitrobenzene is supplied to the reaction zone at one time.

* * * * *